United States Patent [19]

Kanou et al.

[11] Patent Number: 5,756,768
[45] Date of Patent: May 26, 1998

[54] PROCESS FOR PREPARING CARBOXYLIC ACID DERIVATIVE

[75] Inventors: Fumihiko Kanou, Himeji; Toshihiro Takeda, Kobe; Natsuki Mori, Takasago; Kazunori Kan, Nishomiya, all of Japan

[73] Assignee: Kanegafuchi Kagaku Kogyo Kabushiki Kaisha, Osaka, Japan

[21] Appl. No.: 693,230

[22] PCT Filed: Dec. 25, 1995

[86] PCT No.: PCT/JP95/02674

§ 371 Date: Aug. 22, 1996

§ 102(e) Date: Aug. 22, 1996

[87] PCT Pub. No.: WO96/20189

PCT Pub. Date: Jul. 4, 1996

[30] Foreign Application Priority Data

Dec. 28, 1994 [JP] Japan ................................. 6/329090

[51] Int. Cl.⁶ ........................ C07D 333/32; C07D 333/34
[52] U.S. Cl. ........................ 549/66; 549/62; 549/28
[58] Field of Search ........................ 549/66, 62, 28

[56] References Cited

U.S. PATENT DOCUMENTS

| | | | |
|---|---|---|---|
| 4,021,450 | 5/1977 | Ahrens et al. | 549/66 |
| 4,797,143 | 1/1989 | Baldwin et al. | 514/432 |
| 4,968,814 | 11/1990 | Blacklock et al. | 549/66 |
| 4,968,815 | 11/1990 | Blacklock et al. | 549/66 |
| 5,474,919 | 12/1995 | Chartrain et al. | 435/118 |
| 5,574,176 | 11/1996 | Mathre et al. | 549/66 |

OTHER PUBLICATIONS

Blacklock et al., "An Enantioselective Synthesis of Topically–Active Carbonic Anhydrase Inhibitor MK—0507," J. Org. Chem. 58, 1672–79, 1993.

Primary Examiner—Deborah Lambkin
Attorney, Agent, or Firm—Armstrong, Westerman, Hattori, McLeland & Naughton

[57] ABSTRACT

There is described a process for preparing 3-(2-thienylthio) butyric acid by converting a compound having the formula (III):

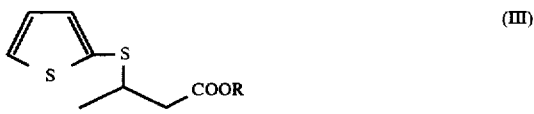

wherein R is a straight chain or branched $C_1$ to $C_4$ alkyl group, whereby the production of 3-(3-thienylthio)butyric acid as a by-product which is the position isomer can be controlled to at most 0.1 mol %. 3-(2-Thienylthio)butyric acid is a useful compound as an intermediate for a medicinal compound.

12 Claims, 1 Drawing Sheet

PROCESS FOR PREPARING CARBOXYLIC ACID DERIVATIVE

This application is a 371 of PCT/JP95/02674 Dec. 29, 1995.

TECHNICAL FIELD

The present invention relates to a process for preparing 3-(2-thienylthio)butyric acid having the formula (I):

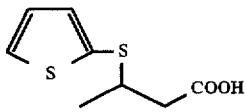
(I)

The present compound is a compound as an important key intermediate in the preparation of a medicament having the formula (V):

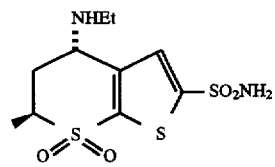
(V)

which is used in the treatment of glaucoma, MK-507 (see Fortschritte der Ophthalmologie, 88, 513 (1991)).

BACKGROUND ART

As a process for preparing 3-(2-thienylthio)butyric acid, there is known a process wherein 3-(2-thienylthio)butyric acid methyl ester is hydrolyzed with an about 6 mol/l aqueous solution of hydrochloric acid of which hydrogen ion concentration is about 6 mol/l under refluxing conditions (see Journal of Organic Chemistry, 58 [7], 1672 (1993), U.S. Pat. No. 4,968,814 and Japanese Unexamined Patent Publication No. 224576/1992).

However, in the above-mentioned process, the production of 3-(3-thienylthio)butyric acid having the formula (II):

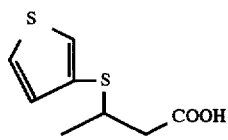
(II)

as a by-product is unavoidable. Furthermore, the removal of this by-product is extremely difficult because in the subsequent process for the synthesis of the medicament used in the treatment of glaucoma having the formula (V), this by-product is subjected to the chemical conversion in the same way as in 3-(2-thienylthio)butyric acid.

Therefore, in order to use the obtained 3-(2-thienylthio)butyric acid as an intermediate for a medicament, it has been desired to develop a process for preparing 3-(2-thienylthio)butyric acid wherein the content of 3-(3-thienylthio)butyric acid is controlled to at most 0.1 mol %.

DISCLOSURE OF THE INVENTION

As the result of the detailed investigation of the present inventors to control the production of 3-(3-thienylthio)butyric acid as a by-product, they have found a process for preparing 3-(2-thienylthio)butyric acid whereby the production of 3-(3-thienylthio)butyric acid as a by-product can be dramatically controlled to at most 0.1 mole % by controlling the concentration of an aqueous solution of acid to be used and, preferably, the kind of the acid. Consequently, the present invention has been accomplished.

Namely, the present invention relates to a process for preparing a compound having the formula (I):

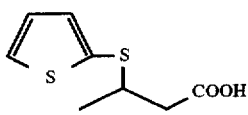
(I)

characterized by reacting a compound having the formula (III).

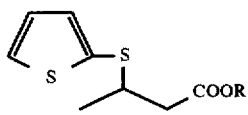
(III)

wherein R is a straight chain or branched $C_1$ to $C_4$ alkyl group, with an aqueous solution of acid having a hydrogen ion concentration of at most 3.9 mol/l at a temperature of not more than reflux temperature of reaction mixture whereby the production of a by-product compound having the formula (II):

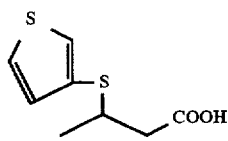
(II)

is controlled to at most 0.1 mol %.

BEST MODE FOR CARRYING OUT THE INVENTION

Figure 1:
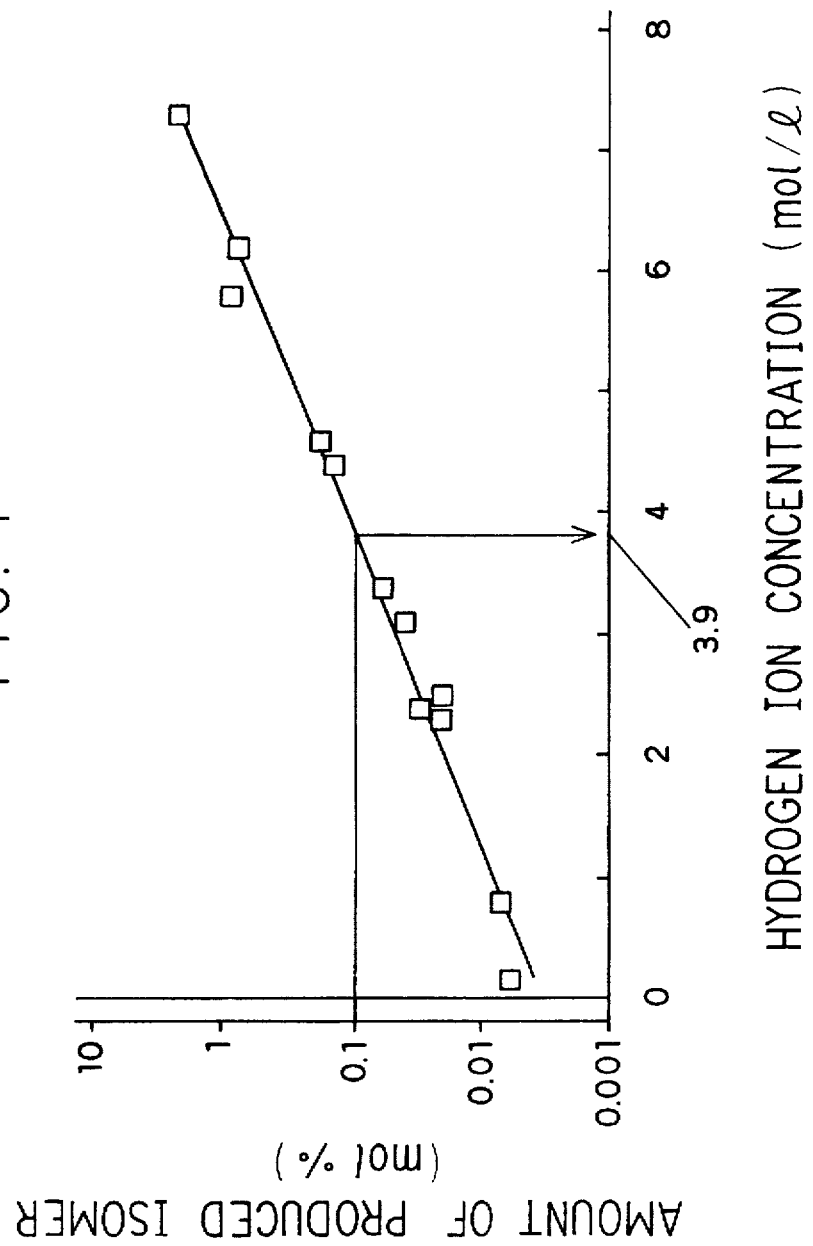
FIG. 1 is a graph showing the relationship between an amount of 3-(3-thienylthio)butyric acid produced after 24 hours of reaction and a hydrogen ion concentration (mol/l) of an aqueous solution of acid in Examples 1 to 7 and Reference Examples 1 to 5.

The compound having the formula (III) as a starting compound can be prepared according to the process described in U.S. Pat. No. 4,968,814.

To be concrete, the compound (III) can be prepared by reacting an alkaline metal salt of 2-thiophenethiol with a 3-tosyloxybutyric acid ester.

Examples of the group represented by R in the formula (III) are, for instance, methyl group, ethyl group, n-propyl group, i-propyl group, n-butyl group, i-butyl group, sec-butyl group, tert-butyl group and the like. Among these, methyl group is preferable from the viewpoint that an alcohol component produced during the reaction is easily removed by distillation.

Examples of the acid in the aqueous solution of acid to be used are, for instance, an inorganic acid such as hydrochloric acid, sulfuric acid, phosphoric acid, hydrobromic acid, hydroiodic acid or hydrofluoric acid, and an organic acid such as trifluoroacetic acid, toluenesulfonic acid or methanesulfonic acid. It is desirable to use hydrochloric acid or sulfuric acid because it is easy to industrially handle them in the waste disposal etc.

The concentration of the aqueous solution of acid to be used can be determined at an optional concentration of a hydrogen ion concentration of at most 3.9 mol/l. The hydrogen ion concentration can easily be obtained by multiplication of a degree of dissociation calculated from a dissociation constant Ka by the acid concentration equal to the concentration of an aqueous solution of acid.

A temperature during the reaction can be determined at an optional temperature of between 25° C. and not more than the reflux temperature of the reaction mixture, and may be decided taking account of the acceptable reaction time.

In the case of carrying out the reaction as it is, the reaction reaches equilibrium in a conversion ratio which depends on the charging amount of the compound having the general formula (III), the kind of the acid and the concentration of the aqueous solution of acid to be used. However, it is possible to raise the conversion ratio up to any desired conversion ratio by removing the produced alcohol component by distillation. Additionally, in the case that at this time, water is also removed by distillation together with the alcohol component, water may be added to the reaction system so that the determined hydrogen ion concentration can be maintained.

The obtained 3-(2-thienylthio)butyric acid may be isolated and purified by a usual treating process such as solvent extraction, concentration or distillation, or may be used as it is.

The present invention is more specifically explained below by means of the Examples. However, it is to be understood that the present invention is not limited to those Examples.

REFERENCE EXAMPLE 1

There were mixed 180 g of a concentrated hydrochloric acid having a concentration of 35% and 146 g of water to prepare an aqueous solution of hydrochloric acid which is a 5.8 mol/l aqueous solution of hydrochloric acid and has a hydrogen ion concentration of 5.8 mol/l and of which amount is 326 g.

The aqueous solution of hydrochloric acid was mixed with 56 g of 3-(2-thienylthio)butyric acid methyl ester (not content 54 g), with stirring at room temperature. The mixture was warmed till the contents started to be refluxed and then was allowed to react under refluxing conditions for 24 hours. The progress of the reaction was monitored by means of a high-pressure liquid chromatography. The conversion ratio was 99 mol % and the amount of 3-(3-thienylthio)butyric acid produced was 0.82 mol % (mol % based on 3-(2-thienylthio)butyric acid).

The high-pressure liquid chromatography was carried out under the following conditions:

Column: Finepak SIL $C_{18-5}$ (4.6 mm×25 cm, made by JASCO CORP.)

Eluent: acetonitrile: water: phosphoric acid =4: 6: 0.006 (V/V)

Flow rate: 1.0 ml/min

Temperature: 40° C.

Detection condition: U.V. detector, wavelength: 230 nm (2-Thienylthio)butyric acid $^1$H NMR (CDCl$_3$) 7.41 (M, 1H), 7.17 (M, 1H), 7.02 (M, 1H), 3.37 (M, 1H), 2.71 (dd, 1H, J=16.0, J=6.4 Hz), 2.47 (dd, 1H, J=16.0, J=8.0 Hz), 1.34 (d, 3H, J=6.8 Hz)

$^{13}$C NMR (CDCl$_3$) 177.5 (s), 136.4 (s), 130.9 (s), 130.5 (s), 127.7 (s), 41.4 (s), 41.3 (s), 20.7 (s)

3-(3-Thienylthio)butyric acid $^1$H NMR (CDCl$_3$) 7.35 (M, 2H), 7.08 (M, 1H), 3.45 (M, 1H), 2.65 (dd, 1H, J=15.6, J=6.4 Hz), 2.47 (dd, 1H, J=15.6, J=8.4 Hz), 1.33 (d, 3H, J=7.6 Hz)

$^{13}$C NMR (CDCl$_3$) 177.6 (s), 132.2 (s), 129.1 (s), 128.3 (s), 126.2 (s), 41.6 (s), 39.6 (s), 20.9 (s)

Example 1

There were mixed 26 g of a concentrated hydrochloric acid having a concentration of 35% and 308 g of water to prepare an aqueous solution of hydrochloric acid which is a 0.8 mol/l aqueous solution of hydrochloric acid and has a hydrogen ion concentration of 0.8 mol/l and of which the amount is 334 g. The aqueous solution of hydrochloric acid was mixed with 56 g of 3-(2-thienylthio)butyric acid methyl ester (net content 54 g) with stirring at room temperature. The mixture was allowed to react under refluxing conditions for 24 hours. The progress of the reaction was monitored by means of a high-pressure liquid chromatography. The conversion ratio as 65 mol % and the amount of 3-(3-thienylthio)butyric acid produced was 0.007 mol % (mol % based on 3-(2-thienylthio)butyric acid).

The high-pressure liquid chromatography was carried out under the following conditions:

Column: Finepak SIL $C_{18-5}$ (4.6 mm×25 cm, made by JASCO CORP.)

Eluent: acetonitrile: water: phosphoric acid=4: 6: 0.006 (V/V)

Flow rate: 1.0 ml/min

Temperature: 40° C.

Detection condition: U.V. detector, wavelength: 230 nm

In order to further proceed the reaction, 42 g, 83 g and 111 g of the mixture of methanol and water were removed by distillation after 24 hours, 48 hours and 55 hours, respectively. Before removing the mixture after 55 hours, 103 g of water was added. The reaction mixture was allowed to react for 71 hours in total. The conversion ratio was 96 mol % and the amount of 3-(3-thienylthio)butyric acid produced was 0.009 mol % (mol % based on 3-(2-thienylthio)butyric acid).

Each NMR data obtained as to 3-(2-thienylthio)butyric acid and 3-(3-thienylthio)butyric acid was consistent with that obtained in Reference Example 1.

Examples 2 to 7 and Reference Examples 2 to 5

3-(2-Thienylthio)butyric acid was prepared in the same procedure as in Example 1 wherein the charging amount of 3-(2-thienylthio)butyric acid methyl ester, the kind of the acid, the acid concentration and the charging amount of the aqueous solution of acid and the reaction time were changed. In Examples 2 to 7, the hydrogen ion concentration was at most 3.9 mol/l and in Reference Examples 2 to 5, the hydrogen ion concentration was at least 3.9 mol/l.

The results thereof are shown in Table 1.

TABLE 1

| | Charging amount of 3-(2-thienylthio)-butyric acid methyl ester (net content) (g) | Aqueous solution of acid | | | Reaction time (Hr) | Conversion ratio (mol %) | Amount of isomer produced after 24 hours (mol %) | Amount of isomer produced at end of reaction (mol %) |
|---|---|---|---|---|---|---|---|---|
| | | Kind of acid | Acid concentration (mol/l) | Amount (g) | Hydrogen ion concentration (mol/l) | | | | |
| Ex. | | | | | | | | | |
| 2 | 54 | Hydrochloric acid | 2.4 | 326 | 2.4 | 28 | 79 | 0.03 | 0.03 |
| 3 | 54 | Sulfuric acid | 2.3 | 352 | 2.5 | 28 | 65 | 0.02 | 0.02 |
| 4 | 54 | Sulfuric acid | 2.8 | 352 | 3.1 | 30 | 67 | 0.04 | 0.04 |
| 5 | 54 | Trifluoroacetic acid | 6.4 | 280 | 3.4 | 28 | 99 | 0.06 | 0.07 |
| 6 | 43 | Trifluoroacetic acid | 4.3 | 376 | 2.3 | 28 | 94 | 0.02 | 0.02 |
| 7 | 43 | Phosphoric acid | 2.0 | 262 | 0.16 | 28 | 28 | 0.006 | 0.006 |
| Ref. Ex. | | | | | | | | | |
| 2 | 34 | Hydrochloric acid | 4.4 | 201 | 4.4 | 27 | 93 | 0.14 | 0.16 |
| 3 | 26 | Sulfuric acid | 4.2 | 200 | 4.6 | 27 | 66 | 0.18 | 0.20 |
| 4 | 54 | Sulfuric acid | 5.6 | 194 | 6.2 | 28 | 60 | 0.74 | 0.74 |
| 5 | 20 | Sulfuric acid | 6.6 | 201 | 7.3 | 27 | 75 | 2.10 | 2.13 |

Hydrogen ion concentration

=(acid concentration)×(degree of dissociation)

Hydrochloric acid:
  Dissociation constant $Ka=10^8$ (25° C.)
  Degree of dissociation=1.00

Sulfuric acid:
  Dissociation constant $Ka_1=\infty$ (25° C.)
  Dissociation constant $Ka_2=0.01$ (25° C.)
  Degree of dissociation=1.10

Trifluoroacetic acid:
  Dissociation constant $Ka=0.59$ (25° C.)
  Degree of dissociation=0.53

Phosphoric acid:
  Dissociation constant $Ka_1=7.4\times10^{-3}$ (25° C.)
  Degree of dissociation=0.08

The relationship between the amount of 3-(3-thienylthio) butyric acid produced after 24 hours of reaction and the hydrogen ion concentration (mol/l) of the aqueous solution of acid in Examples 1 to 7 and Reference Examples 1 to 5 is shown in FIG. 1. From this graph, it is clear that the amount of the isomer 3-(3-thienylthio)butyric acid to be produced can be controlled to at most 0.1 mol % by use of the aqueous solution of acid having a hydrogen ion concentration of at most 3.9 mol/l.

INDUSTRIAL APPLICABILITY

According to the present invention, 3-(2-thienylthio) butyric acid which is an important intermediate for a medicament used in the treatment of glaucoma MK-507, can be prepared with controlling the content of contamination by 3-(3-thienylthio)butyric acid, which is the position isomer, to at most 0.1 mol %.

We claim:

1. A process for preparing a compound having the formula (I):

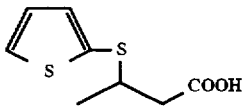

characterized by reacting a compound having the formula (III):

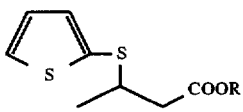

wherein R is a straight chain or branched $C_1$ to $C_4$ alkyl group, with an aqueous solution of acid having a hydrogen ion concentration of at most 3.9 mol/l at a temperature of not more than reflux temperature of reaction mixture whereby the production of a by-product compound having the formula (II):

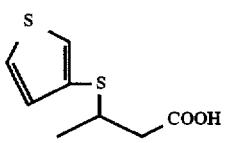

is controlled to at most 0. 1 mol %.

2. The process of claim 1 wherein R in the formula (III) is methyl group.

3. The process of claim 1, characterized by removing an alcohol component by distillation, which is produced during the reaction and has the formula (IV):

R—OH     (IV)

wherein R is a straight chain or branched $C_1$ to $C_4$ alkyl group.

4. The process of claim 2, characterized by removing an alcohol component by distillation, which is produced during the reaction and has the formula (IV):

$$R-OH \quad (IV)$$

wherein R is a straight chain or branched $C_1$ to $C_4$ alkyl group.

5. The process of claim 1 wherein the acid is hydrochloric acid.

6. The process of claim 2 wherein the acid is hydrochloric acid.

7. The process of claim 3 wherein the acid is hydrochloric acid.

8. The process of claim 4 wherein the acid is hydrochloric acid.

9. The process of claim 1 wherein the acid is sulfuric acid.

10. The process of claim 2 wherein the acid is sulfuric acid.

11. The process of claim 3 wherein the acid is sulfuric acid.

12. The process of claim 4 wherein the acid is sulfuric acid.

\* \* \* \* \*